(12) United States Patent
Holst et al.

(10) Patent No.: US 6,462,181 B1
(45) Date of Patent: Oct. 8, 2002

(54) PROCESS FOR PREPARING A KAPPA-CASEINO GLYCOMACROPEPTIDE OR A DERIVATIVE THEREOF

(75) Inventors: Hans Henrik Holst, Videbæk; Dereck E. W. Chatterton, Århus V, both of (DK)

(73) Assignee: Arla Foods Amba, Viby J. (DK)

( * ) Notice: Subject to any disclaimer, the term of this patent is extended or adjusted under 35 U.S.C. 154(b) by 0 days.

(21) Appl. No.: 09/581,294

(22) PCT Filed: Dec. 9, 1998

(86) PCT No.: PCT/DK98/00543
§ 371 (c)(1),
(2), (4) Date: Jul. 21, 2000

(87) PCT Pub. No.: WO99/29183
PCT Pub. Date: Jun. 17, 1999

(30) Foreign Application Priority Data

Dec. 11, 1997 (DK) .............................. 1441/97

(51) Int. Cl.⁷ .................................. C07K 1/34
(52) U.S. Cl. ................ 530/414; 530/360; 530/361; 530/395; 530/412
(58) Field of Search ................ 530/412, 414, 530/395, 360, 361

(56) References Cited

U.S. PATENT DOCUMENTS

| | | | | |
|---|---|---|---|---|
| 3,323,963 A | * | 6/1967 | Summers | 156/192 |
| 4,125,527 A | | 11/1978 | Buhler et al. | 260/112 R |
| 4,994,441 A | | 2/1991 | Neeser | 514/8 |
| 5,063,203 A | | 11/1991 | Drouet et al. | 514/8 |
| 5,075,424 A | | 12/1991 | Tanimoto et al. | 530/361 |
| 5,830,360 A | * | 11/1998 | Mozayeni | 210/651 |

FOREIGN PATENT DOCUMENTS

| | | |
|---|---|---|
| EP | 0 393 850 A2 | 10/1990 |
| EP | 0 488 589 B1 | 6/1992 |
| EP | 0453782 * | 1/1994 |
| WO | 94/15952 | 7/1994 |

\* cited by examiner

Primary Examiner—Christopher S. F. Low
Assistant Examiner—David Lukton
(74) Attorney, Agent, or Firm—Finnegan, Hnderson, Farabow, Garrett & Dunner, L.L.P.

(57) ABSTRACT

Improved process for preparing a kappa-caseino glycomacropeptide which comprises adjusting the pH of a solution of a milk starting material to below 4, cold ultrafiltration and concentration of the starting material on a spiral filter. This process is usable in industrial scale without fouling problems and without damaging the usable milk material by-product.

22 Claims, No Drawings

PROCESS FOR PREPARING A KAPPA-CASEINO GLYCOMACROPEPTIDE OR A DERIVATIVE THEREOF

The present invention relates to an improvement of a process for producing kappa-caseino glycomacropeptide, GMP, κ-caseinoglycopeptide, CGP or caseinomacropeptide, CMP or a derivative thereof without destroying the milk starting material, in particular whey, which is a useful by-product. This improved process is useful in a industrial scale at commercial way - not just useful in the laboratory.

GMP has numerous useful possible applications.

U.S. Pat. No. 4,994,441 proposed to use GMP in a composition for treating and inhibiting formation of dental plaque and caries, for example in a tooth paste.

U.S. Pat. No. 5,063,203 proposed to use κ-caseinoglycopeptide for the manufacture of a composition, in particular a medicament, for the prevention and/or the treatment of thrombi.

Further GMP or CGP has been proposed to stimulate bifido-bacterial growth making it useful in dietetic food products i.a. for infants, and prevention of binding of cholera toxin to its receptor.

GMP has also been suggested for use in the treatment of disorders in amino acid metabolism, such as phenylke-touria (PKU).

Many attempts have been undertaken to find useful processes to prepare GMP. Most of them are not industrially usable.

WO 94/15952 relates to a method for production of a kap-pa-caseino glycomacropeptide i.a. comprising heat treatment of a whey product. This causes a denaturation of the whey by-product so that it will be unsuitable for other purposes.

EP 0 453 782 has proposed a process for the production of kappa-caseinoglycomacropeptide in which the proteins of a whey product concentrated with proteins partly freed from lactose are flocculated, resulting in a precipitate and a first supernatant, and the first supernatant is concentrated by ultrafiltration, leading to a retentate, which is then treated with ethanol, which produces a precipitate and a second supernatant, the second supernatant is collected and then dried. This process is very inconvenient and troublesome.

EP 0 393 850 and U.S. Pat. No. 5,075,424 relate to a process for producing a kappa-caseino glycomacropeptide which comprises adjusting the pH of a solution of milk starting materials containing the kappa-caseino glycomacropeptide to below 4, treating the solution by ultrafiltration with a membrane passing a molecular weight fraction of 10,000 to 50,000, and concentrating the filtrate obtained with a membrane passing a molecular weight fraction of 50,000 or less.

The concentration can be performed on the same filter by readjustment of pH to 4 or higher, typically 6.5, or on another membrane having a smaller cut-off value under 10,000.

This known process has a high production cost, gives an impure product, and the filter is fast fouled during the filtration by protein and must often be cleaned. The process gives a poor yield. A diluted starting solution is used in order to reduce fouling. The diluted starting solution requires use of large amounts of water and more energy. A typical starting solution is a solution having a protein content of 2% by weight.

EP 0 488 589 relates to a process for producing a kappa-caseino glycomacropeptide comprising contacting milk raw materials containing the kappa-caseino glycomacropeptide with an ion exchanger, collecting a fraction which does not adsorb on the ion exchanger, and concentrating and desalting the fraction to obtain the kappa-caseino glycomacropeptide. This process is rather convenient because it is easy to perform and it does not damage the whey by-product. However deposits on the ion exchanger are a problem, so it has to be cleaned and replaced rather often. The applicant of EP 0 393 850 tries to overcome the problem of protein fouling during filtration by removing proteins by this process using an ion exchanger.

It has now surprisingly been shown that an improvement of the process known from EP 0 393 850 as stated in the following, prevents the drawbacks of the known processes.

The process according to the invention is of the known type which comprises adjusting the pH of a solution of milk starting materials containing the kappa-caseino glycomacropeptide or derivatives thereof to below 4, treating the solution by ultrafiltration with a membrane passing a molecular weight fraction of 10,000 to 50,000, and after adjustment of pH to above 4 concentrating the filtrate obtained with a membrane passing a molecular weight fraction of 50,000 or less. The process of the invention is characterized in that cold ultrafiltration is applied using a spiral filter.

The process of the invention gives a pure product in a high yield and at a low cost without denaturing the valuable whey by-product. The process gives a better bacteriological control.

Ultrafiltration is preferably carried out at a temperature below 15° C., especially 7 to 15° C. For the time being it is preferred to use about 12° C.

The starting material can be a whey product. It is preferred to use a concentrated whey product, such as a whey product having a content of above 15, especially 35 to 80 and most preferred 85 to 95% by weight protein based on the dry matter content. Preferred whey products are whey protein concentrate, WPC and whey protein isolate, WPI. Consequently is it possible to reduce the amount of energy and water needed in the process The process of the invention can be carried out using a concentration of 0.8 to 15% by weight of protein , 5 to 15, especially 6 to 8% by weight is preferred. For the time being 7% by weight is the most preferred concentration.

A FV membrane from OSMONICS-DESALINATION, Vista, Calif., USA is a usable membrane. Other firms have corresponding membranes usable in the invention.

The ultrafiltration can be improved by using a filter aid. It is surprising that calcium phosphate can be used, because one should expect that it had a tendency to dissolve in the acid solution. It is preferred to use milk based calcium phosphate, especially if the GMP prepared by the invention has to be used in food or the like.

The ultrafiltration can be carried out at a pH of 2.5 to 3.5, 2.8 to 3.2 being a preferred range, and for the time being a pH of 3.0 is preferred.

The invention is further illustrated by the following examples.

EXAMPLE 1

250 litres of WPC concentrate containing 30% dry matter and 23% protein was diluted with 750 litres of demineralized cold water, which left 7.50% dry matter and 5.75% protein in the dilution. 12 N hydrochloric acid was added until the pH was 3.1.

Ultrafiltration I:

The solution was filtered on two UF spiral elements of the type FV6338C from OSMONICS-DESALINATION having a cut-off value of 20,000 Daltons. Before the filtration the membranes were coated with 500 g of suspended calcium phosphate product. The total membrane area was 31 m². The filtration was carried out under the following conditions: The temperature was maintained at approximately 15° C., the mean pressure was maintained at 3 bars with a feeding pressure of 2 bars. The pH was maintained at 3.1 by using 12 N HCl, and cold demineralized water was added with the same flow as permeate was removed. The recirculation flow in the loop was 16 m³/h, and the recirculation over the feeding tank was approximately 5 m³/h. After a 7 hour filtration the addition of demineralized water to the feeding tank was stopped. Subsequently a concentration was carried out until the dry matter in the feeding tank was 15%. The mean flux was measured to 36.1 l/m²h. 28% sodium hydroxide was added to the permeate until the pH was 6.7.

Ultrafiltration II:

The pH adjusted permeate from ultrafiltration I was then ultrafiltrated at pH 6.7 on two ultrafiltration spiral elements of the type HFK328 6338NYT from KOCK, Wilmington, Mass., USA having a cut-off value of 5,000 Daltons. The filtration was carried out under the following conditions: The temperature was maintained at 15° C., the mean pressure was maintained at 4 bars. Same flow as under ultrafiltration I. After concentration a diafiltration was carried out to demineralize the solution. After filtration the concentrate was dried in a pilot spray dryer. 5.0 kg of powder having the composition indicated in the subsequent table was obtained.

EXAMPLE 2

200 litres of WPC concentrate containing 30% dry matter and 23% protein was diluted with 400 litres of demineralized cold water, which left 10.00% dry matter and 7.67% protein in the dilution. 12 N hydrochloric acid was added until the pH was 2.8.

Ultrafiltration I:

The solution was filtrated on two ultrafiltration spiral elements of the type FV6338C from OSMONICS-DESALINATION having a cut-off value of 20,000 Daltons. Before the filtration the membranes were coated with 500 g of suspended calcium phosphate product. The total membrane area was 31 m². The filtration was carried out under the following conditions: The temperature was maintained at approximately 12° C., the mean pressure was maintained at 3.5 bars with a feeding pressure of 2.5 bars. The pH was maintained at 3.0 by using 12 N HCl, and demineralized cold water was added with the same flow as permeate was removed. The recirculation flow in the loop was 16 m³/h, and the recirculation over the feeding tank was approximately 5 m³/h. After an eight-hour filtration the filtration was stopped. The mean flux was 21.1 l/m² h. 28% sodium hydroxide was added to the permeate until the pH was 6.7.

Ultrafiltration II:

The pH adjusted permeate from ultrafiltration I was ultrafiltrated at pH 6.7 on two ultrafiltration spiral elements of the type HFK328 6338NYT from KOCK having a cut-off value of 5,000 Daltons. The filtration was carried out under the following conditions: The temperature was maintained at 12° C., the mean pressure was maintained at 4 bars. Same flow as under ultrafiltration I. After concentration a diafiltration was carried out to demineralize the solution. After filtration the concentrate was dried in a pilot spray dryer. 4.2 kg of powder containing 79.5% protein was obtained, the 90% being GMP.

COMPARATIVE EXAMPLES

In the two subsequent tests, which are comparative tests, it has been attempted to repeat example 1 of the EP 0 393 850 patent as far as possible: 100 litres of WPC concentrate containing 30% dry matter and 23% protein was diluted with 1300 litres of demineralized water heated to 55° C., which left 2.14% dry matter and 1.64% protein in the dilution. 12 N hydrochloric acid was added until the pH was 3.5.

Ultrafiltration I:

The solution was filtered on a module 38 from DDS fitted with GR61PP membranes from DOW with a cut-off value of 20,000 Daltons. The module has an area of 42 m² divided in five sections. The filtration was carried out under the following conditions: The temperature was maintained at 50° C., the mean pressure was maintained at 4 bars, the pH was maintained at 3.5 by using 12 N hydrochloric acid, and 50° C. hot demineralized water was added to the feeding tank at a speed of 90% of the permeate flow so that the concentration of dry matter and protein in the feeding tank was increasing very slowly. The recirculation in the loop was 42 m³/h, and the recirculation over the feeding tank was approximately 5 m³/h.

When 8000 litres of permeate has been removed, the filtration was stopped. The mean flux was measured to 46.7 l/m²h. 28% sodium hydroxide was added to the permeate until the pH was 7.0.

Ultrafiltration II:

The pH adjusted UFI permeate from ultrafiltration I was then ultrafiltrated in the same plant again at 50° C., the mean pressure being maintained at 4 bars, and the pH being maintained at 7.0 by using sodium hydroxide. Same flow as under ultrafiltration I. The concentrate was diafiltered in order to demineralize the solution. After filtration the concentrate was dried in a pilot spray dryer.

EXAMPLE 3

A GMP powder was prepared by means of the same procedure as described in example 1 of EP 0 393 850.

A DDS module 38 UF plant fitted with GR61PP membranes was used for the test. The membranes had been in use for approximately 200 hours exclusively with whey protein products. In the patent EP 0 393 850 it is stated that when this procedure is followed, a GMP product having a purity of 82% was obtained.

3.3 kg powder having the composition described in the table below was obtained.

EXAMPLE 4

Example 3 was repeated at a temperature of 10–15° C. instead of at the preferred temperature of 50° C. The test was carried out in the same plant fitted with the same membranes.

The GMP powders have the following composition and are here compared with a standard WPC product LACPRODAN-80 and a GMP product obtained by means of the process according to the invention.

TABLE

|  | Product according to example 3 | Product according to example 4 | Standard product | Product according to example 1 (of the invention) |
| --- | --- | --- | --- | --- |
| Dry matter | 92.8 | 92.7 | 94.7 | 94.3 |
| Protein | 81.0 | 80.2 | 77.7 | 79.2 |
| Protein/dry matter | 87.3 | 86.5 | 82.0 | 84.0 |
| Fat | 6.22 | 5.62 | 6.30 | 0.13 |
| Lactose | 0.03 | 0.29 | 5.20 | 0.05 |

TABLE-continued

|  | Product according to example 3 | Product according to example 4 | Standard product | Product according to example 1 (of the invention) |
|---|---|---|---|---|
| pH | 6.23 | 6.56 | 6.46 | 6.45 |
| Mineral | 2.71 | 2.90 | 2.63 | 6.89 |
| Phosphorus | 0.339 | 0.330 | 0.310 | 0.576 |
| Chloride | <0.05 | <0.05 | <0.05 | <0.05 |
| Calcium | 0.533 | 0.423 | 0.380 | 0.979 |
| Potassium | 0.106 | 0.125 | 0.600 | 2.310 |
| Magnesium | 0.076 | 0.057 | 0.064 | 0.133 |
| Sodium | 0.423 | 0.598 | 0.190 | 0.091 |
| α-la | 12.3 | 11.4 | 9.8 | 3.4 |
| β-lg | 47.8 | 46.8 | 39.0 | <0.5 |
| NPN % of protein | 24.6 | 30.7 | 23.9 | >96 |
| Sialic acid/protein | 1.79 | 2.37 | 1.56 | 5.55 |

As is seen, the difference between the product according to example 3 and the standard product is that there is more protein and less lactose in the product prepared according to EP 0 393 850 than in the standard product. The contents of the other components are on the whole the same in the two products both as regards sialic acid and NPN (=GMP+PP). The NPN analysis gives the amount of GMP in the products due to lack of proteose peptone, PP. The reason why the GMP product obtained according to EP 0 393 850 is not as pure as the patent claims, is that we have employed "used" membranes. If we had inserted new membranes before the test, we had no doubt obtained a "purer" product, since it is known to the inventor of the present application that DOW's plate and frame membranes, such as GR61PP, rapidly change their filtration properties, especially in the case of hot filtration (50° C.). During the first filtration the permeate should consist of "pure" GMP. However, from the FPLC chromatograms both α-lactalbumin, α-la and β-lactoglobolin, β-lg are seen in the permeate. During the second filtration some of the GMP is on the other hand lost to the permeate as the membranes are not tight enough owing to pin point holes. From this test it can be concluded that if attempts are made to produce GMP according to the procedure mentioned in EP 0 393 850 on GR61PP membranes which are not new, a product which does not differ essentially from a standard product is obtained.

As appears from the analytical results, the product according to example 1 is very different from the two other products (example 3 and 4) as far as the protein composition is concerned (high concentration of NPN and very low concentration of α-la and β-lg); The mineral content is also very different, more than double the amount of mineral content. It is known that GMP binds large quantities of minerals.

DIFFERENCES BETWEEN THE PROCESS ACCORDING TO EP 0 393 850 (EXAMPLE 3) AND THE PROCESS ACCORDING TO THE INVENTION (EXAMPLES 1 and 2).

The process of the invention as illustrated in the examples 1 and 2 differs from the known process on the following points:

The temperature:

The process of the invention use cold filtration (typically temperatures below 15° C.), whereas all the examples in EP 0 393 850 uses hot filtration (50° C.). When using cold filtration, the membranes last longer, and the retention is also a good deal different (more tight membranes). Moreover, the bacteriological quality is better when cold filtration is used. To prove that cold filtration is better, we have made the test described in example 4. From the results it appears that the NPN (=GMP+PP) content has increased from 24.6% to 30.7% of the protein content. This indeed proves that a purer product is obtained by cold filtration than by hot filtration. The greatest difference is that only a little GMP is lost during the concentration.

The membrane:

In all the examples in EP 0 393 850 use was made of DOW GR61PP membranes on the plate and frame system. This system was the prevailing system in the period where they invented the process. The GR61PP membranes have a bad mechanical durability. The examples of invention make use of a very special membrane: FV from OSMONICS-DESALINATION which has shown a very good mechanical stability. The same permeability was observed after one year of use, as when it was installed in a plant which was in production 24 hours seven days a week.

The feed:

The known process starts with a very weak solution (2% dry matter) and ultra-/diafiltration of this solution, probably because the GMP product becomes more impure if a greater dry matter content is used in the feed. The process of the invention (examples 1 and 2) starts with a dry matter content of approximately 7%. This means that a considerably smaller quantity of water has to be used in order to wash out the same quantity of GMP. The known process uses 12.300 litres/kg GMP. The process of the invention uses 1.880 litres/kg GMP.

Membrane coating:

It has turned out that when the membrane is coated with filter aid, especially with calcium phosphate, before starting the production, the GMP permeability becomes approximately double as large as when the membrane is not coated. To substantiate that coating gives a positive effect, the following two tests were carried out:

EXAMPLE 5

200 litres of WPC retentate with 30% dry matter and 23% protein was diluted with 800 litres of demineralized water, and the pH was adjusted to 3.0 by using 30% hydro-chloric acid.

This solution was filtered on two ultrafiltration spiral elements of the type FV with and without coating with 500 g calcium phosphate under the following conditions:

Temperature: 10–12° C. Booster flow: 16 m$^3$/h. Feeding pressure: 2 bars. Retentate flow to the feeding tank: 5 m3/h. After reaching 7% dry matter diafiltration was carried out with the same flow as the permeate flow. The pH was maintained at 3.0 during the whole filtration. Permeate samples were collected after 5 min. and then after each hour. The samples were analysed on HPLC for GMP and α-lactalbumin.

The following results were obtained:

|  | With Ca$_3$(PO$_4$)$_2$ | | Without Ca$_3$(PO$_4$)$_2$ | |
|---|---|---|---|---|
|  | α-la % | GMP % | α-la % | GMP % |
| 5 min. | 0.010 | 0.207 | 0.010 | 0.088 |
| 1 hour | 0.009 | 0.193 | 0.008 | 0.144 |
| 2 hours | 0.007 | 0.131 | 0.007 | 0.121 |
| 3 hours | 0.009 | 0.121 | 0.008 | 0.117 |

|  | With Ca₃(PO₄)₂ | | Without Ca₃(PO₄)₂ | |
| --- | --- | --- | --- | --- |
|  | α-la % | GMP % | α-la % | GMP % |
| 4 hours | 0.010 | 0.101 | 0.008 | 0.105 |
| 5 hours | 0.009 | 0.080 | 0.013 | 0.122 |

The reason why the GMP content in the permeate with coating fell much towards the end is that there was not much GMP left in the retentate. In the test without coating there was still some GMP left after 5 hours' running. The conclusion is that coating has the effect that GMP can be washed out much quicker than without coating.

ANALYSIS METHODS

The NPN analysis employed differs somewhat from other NPN analysis. The following procedure is used:

1: Dissolve 15 g of powder in 285 g of demineralized water.
2: pH adjust the solution to 6.5 by using 10% HCl or 10% NaOH
3: The solution is analysed for total protein (Kjeldahl).
4: The rest is heat treated in closed glass at 90° C. for 60 min.
5: Cooling to room temperature.
6: pH adjustment to 4.6 by using 30% HCl.
7: Centrifugation at 15,000 g for 10 min.
8: Filter supernatant by means of a non-nitrogen containing filter.
9: The filtrate is analysed for total protein.

$PR_1$=Protein content in the solution before heat treatment.
$PR_2$=Protein content in the filtrate after heat treatment.
NPN protein ($PR_2$.100)/$PR_1$.

What is claimed is:

1. A process for producing a kappa-caseino glycomacropeptide comprising
   (a) adjusting the pH of a solution of milk starting material containing a kappa-caseino glycomacropeptide to below 4;
   (b) subjecting the solution to ultrafiltration at a temperature of about 15° C. or below using a membrane in the form of a spiral filter that passes a molecular weight fraction of 10,000 to 50,000 Daltons to obtain an ultrafiltrate and a retentate;
   (c) adjusting the pH of the ultrafiltrate to above 4;
   (d) concentrating the ultrafiltrate of step (c) at a temperature of about 15° C. or below by means of a membrane that passes a molecular weight fraction of 50,000 Daltons or less.

2. A process according to claim 1 wherein the ultrafiltration is carried out at a temperature below 15° C.
3. A process according to claim 1 wherein the ultrafiltration is carried out at a temperature of 7 to 1 5° C.
4. A process according to claim 3 wherein the temperature is 12° C.
5. A process according to any of claims 1, 3 or 4 wherein the if starting material is a whey product.
6. A process according to claim 5 wherein the starting material is a whey product having a content of above 15% by weight protein based on dry matter.
7. A process according to claim 6 wherein the starting material is a whey product having a content of 35 to 80% by weight protein based on dry matter.
8. A process according to claim 6 wherein the starting material is a whey product having a content of 85 to 95% by weight protein based on dry matter.
9. A process according to claim 5 wherein the starting material is a whey protein concentrate, WPC.
10. A process according to claim 5 wherein the starting material is a whey protein isolate, WPI.
11. A process according to claim 6 wherein the starting material contains from 0.8 to 15% by weight of protein in the solution.
12. A process according to claim 11 wherein the starting material contains from 5 to 15% by weight of protein in the solution.
13. A process according to claim 12 wherein the starting material contains from 6 to 8% by weight of protein in the solution.
14. A process according to claim 13 wherein the starting material contains 7% by weight of protein in the solution.
15. A process according to claim 1 wherein the spiral filter has a if cut-off value of 20,000 Daltons.
16. A process according to claim 1 wherein the ultrafiltration is carried out on a membrane coated with a filter aid.
17. A process according to claim 16 wherein the filter aid is calcium phosphate.
18. A process according to claim 17 wherein the filter aid is milk based calcium phosphate.
19. A process according to claim 1 wherein the ultrafiltration is carried out at a pH of 2.5 to 3.5.
20. A process according to claim 19 wherein the ultrafiltration is carried out at a pH of 2.8 to 3.2.
21. A process according to claim 20 wherein the ultrafiltration is carried out at a pH of 3.0.
22. A process according to claim 1 including isolating the kappa-caseino glycomacropeptide following step (d).

* * * * *

UNITED STATES PATENT AND TRADEMARK OFFICE
CERTIFICATE OF CORRECTION

PATENT NO.    : 6,462,181 B1
DATED         : October 8, 2002
INVENTOR(S)   : Hans Henrik Holst et al.

It is certified that error appears in the above-identified patent and that said Letters Patent is hereby corrected as shown below:

<u>Column 8,</u>
Line 6, "1 5° C." should read -- 15° C. --.
Line 10, after "the" delete "if".
Line 37, after "has a" delete "if".

Signed and Sealed this

Sixth Day of May, 2003

JAMES E. ROGAN
*Director of the United States Patent and Trademark Office*